United States Patent
Gandhi et al.

(10) Patent No.: US 9,808,002 B2
(45) Date of Patent: Nov. 7, 2017

(54) MICROBICIDAL COMPOSITION

(71) Applicants: Dow Global Technologies LLC, Midland, MI (US); Rohm and Haas Company, Philadelphia, PA (US)

(72) Inventors: Usha Gandhi, Hatboro, PA (US); Christine McInnis, Blue Bell, PA (US); Kiran Pareek, Bensalem, PA (US); Paul O. Schook, Lake Zurich, IL (US); Nigel G. Watson, Chadds Ford, PA (US); Terry Michael Williams, Lower Gwynedd, PA (US); Bei Yin, Phoenixville, PA (US)

(73) Assignees: DOW GLOBAL TECHNOLOGIES LLC, Midland, MI (US); ROHM AND HAAS COMPANY, Philadelphia, PA (US)

( * ) Notice: Subject to any disclaimer, the term of this patent is extended or adjusted under 35 U.S.C. 154(b) by 0 days.

(21) Appl. No.: 15/588,946

(22) Filed: May 8, 2017

(65) Prior Publication Data

US 2017/0238540 A1 Aug. 24, 2017

Related U.S. Application Data

(62) Division of application No. 15/026,128, filed as application No. PCT/US2014/058820 on Oct. 2, 2014, now Pat. No. 9,675,064.

(60) Provisional application No. 61/886,336, filed on Oct. 3, 2013.

(51) Int. Cl.
*A01N 31/02* (2006.01)
*A01N 37/06* (2006.01)

(52) U.S. Cl.
CPC ............. *A01N 31/02* (2013.01); *A01N 37/06* (2013.01)

(58) Field of Classification Search
CPC ................................ A01N 31/02; A01N 37/06
See application file for complete search history.

(56) References Cited

U.S. PATENT DOCUMENTS

| | | | |
|---|---|---|---|
| 4,295,932 | A | 10/1981 | Pocius |
| 6,039,965 | A | 3/2000 | Donlan et al. |
| 6,241,898 | B1 | 6/2001 | Wright et al. |
| 2004/0167220 | A1 | 8/2004 | Horst et al. |
| 2006/0285995 | A1 | 12/2006 | Hobbs et al. |
| 2007/0280919 | A1 | 12/2007 | Gorton |
| 2009/0176887 | A1 | 7/2009 | Vlasaty et al. |
| 2009/0298951 | A1 | 12/2009 | Van Etten |
| 2010/0081607 | A1 | 4/2010 | Varineau et al. |
| 2011/0098492 | A1 | 4/2011 | Varineau et al. |
| 2012/0100231 | A1 | 4/2012 | Perla et al. |

FOREIGN PATENT DOCUMENTS

| | | |
|---|---|---|
| CA | 1262084 A | 10/1989 |
| EP | 1454527 A1 | 9/2004 |
| GB | 2138798 A | 10/1984 |

OTHER PUBLICATIONS

Adkins, et al., "Morphology and Stability o fCO 2—in-Water Foams with Nonionic Hydrocarbon Surfactants", Langmuir, vol. 26, No. 8, pp. 5335-5348 (2010) XP55115328.

*Primary Examiner* — Sarah Pihonak
(74) *Attorney, Agent, or Firm* — Kenneth Crimaldi

(57) ABSTRACT

An aqueous microbicidal composition having two components. The first component is a nonionic surfactant with structure: $R^2O(CH_2CH(CH_3)O)_3(CH_2CH_2O)_5H$, where $R^2$ is a mixture of $C_8$-$C_{14}$ linear alkyl groups. The second component is a benzoate or sorbate salt. The weight ratio of the nonionic surfactant to the benzoate or sorbate salt is from 1:0.12 to 1:109.7646.

1 Claim, No Drawings

MICROBICIDAL COMPOSITION

This invention relates to microbicidal compositions containing benzoate or sorbate and a surfactant.

A composition containing 5-chloro-2-methylisothiazolin-3-one, 2-methylisothiazolin-3-one and a nonionic dispersant is disclosed in U.S. Pat. No. 4,295,932. The composition contains a 3:1 mixture of 5-chloro-2-methylisothiazolin-3-one and 2-methylisothiazolin-3-one, and a copolymer of ethylene oxide and propylene oxide which appears to have the same composition as PLURONIC L61 or TERGITOL L61 dispersant. However, there is a need for combinations of microbicides having synergistic activity against various strains of microorganisms to provide effective control of the microorganisms. Moreover, there is a need for such combinations containing lower levels of individual microbicides for environmental and economic benefit. The problem addressed by this invention is to provide such synergistic combinations of microbicides.

STATEMENT OF THE INVENTION

The present invention is directed to a synergistic microbicidal composition comprising: (a) a nonionic surfactant with structure:

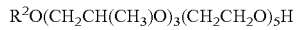

where $R^2$ is a mixture of $C_8$-$C_{14}$ linear alkyl groups; and (b) a benzoate or sorbate salt; wherein a weight ratio of said nonionic surfactant to the benzoate or sorbate salt is from 1:0.12 to 1:109.7646.

The present invention is further directed to a synergistic microbicidal composition comprising: (a) a nonionic surfactant with structure:

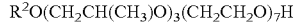

where $R^2$ is a mixture of $C_8$-$C_{14}$ linear alkyl groups; and (b) a benzoate or sorbate salt; wherein a weight ratio of said nonionic surfactant to the benzoate salt is from 1:3.6010 to 1:109.7646 and a ratio of said nonionic surfactant to the sorbate salt is from 1:0.06 to 1:0.5714 or 1:2.3990 to 1:109.7646.

The present invention is further directed to a synergistic microbicidal composition comprising: (a) a nonionic surfactant with structure:

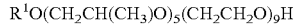

where $R^1$ is a $C_8$ alkyl group; and (b) a sorbate salt; wherein a weight ratio of said nonionic surfactant to the sorbate salt is from 1:0.1 to 1:0.9143.

The present invention is further directed to methods for inhibiting the growth of microorganisms in aqueous media by adding to an aqueous medium a nonionic surfactant as described herein and a benzoate or sorbate salt in the ratios described herein.

DETAILED DESCRIPTION OF THE INVENTION

As used herein, the following terms have the designated definitions, unless the context clearly indicates otherwise. The term "microbicide" refers to a compound capable of inhibiting the growth of or controlling the growth of microorganisms; microbicides include bactericides, fungicides and algaecides. The term "microorganism" includes, for example, fungi (such as yeast and mold), bacteria and algae. The following abbreviations are used throughout the specification: ppm=parts per million by weight (weight/weight), mL=milliliter. Unless otherwise specified, temperatures are in degrees centigrade (° C.), references to percentages are percentages by weight (wt %) and amounts and ratios are on an active ingredient basis, i.e., total weight of benzoate or sorbate salt and the nonionic surfactant. Numbers of polymerized units of propylene oxide or ethylene oxide are number averages.

Preferably, the benzoate or sorbate salt is an alkali metal salt; preferably lithium, sodium or potassium; preferably sodium or potassium. Preferably, the benzoate salt is sodium benzoate. Preferably, the sorbate salt is potassium sorbate. The term "benzoate or sorbate salt" encompasses mixtures of benzoate and sorbate salts.

Preferably, the weight ratio of the nonionic surfactant with structure:

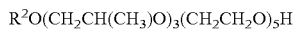

where $R^2$ is a mixture of $C_8$-$C_{14}$ linear alkyl groups to the benzoate salt is from 1:0.5 to 1:100. Preferably, the weight ratio of the nonionic surfactant with structure:

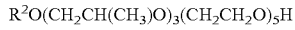

where $R^2$ is a mixture of $C_8$-$C_{14}$ linear alkyl groups to the sorbate salt is from 1:1 to 1:100. Preferably, the weight ratio of the nonionic surfactant with structure:

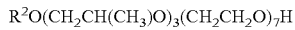

where $R^2$ is a mixture of $C_8$-$C_{14}$ linear alkyl groups to the sorbate salt is from 1:5 to 1:100.

The present invention is further directed to a method for inhibiting the growth of S. aureus in an aqueous medium by adding: (a) a nonionic surfactant with structure:

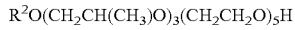

where $R^2$ is a mixture of $C_8$-$C_{14}$ linear alkyl groups; and (b) a benzoate or sorbate salt; wherein a weight ratio of said nonionic surfactant to the benzoate or sorbate salt is from 1:2.9982 to 1:109.7646.

The present invention is further directed to a method for inhibiting the growth of mold, preferably A. niger, in an aqueous medium by adding: (a) a nonionic surfactant with structure:

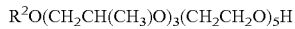

where $R^2$ is a mixture of $C_8$-$C_{14}$ linear alkyl groups; and (b) a benzoate or sorbate salt; wherein a weight ratio of said nonionic surfactant to the benzoate or sorbate salt is from 1:0.12 to 1:13.7143.

The present invention is further directed to a method for inhibiting the growth of S. aureus in an aqueous medium by adding: (a) a nonionic surfactant with structure:

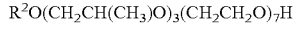

where $R^2$ is a mixture of $C_8$-$C_{14}$ linear alkyl groups; and (b) a benzoate salt; wherein a weight ratio of said nonionic surfactant to the benzoate salt is from 1:3.6010 to 1:109.7646; preferably from 1:10.2886 to 1:109.7646.

The present invention is further directed to a method for inhibiting the growth of S. aureus in an aqueous medium by adding: (a) a nonionic surfactant with structure:

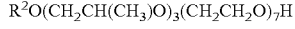

where $R^2$ is a mixture of $C_8$-$C_{14}$ linear alkyl groups; and (b) aسorbate salt; wherein a weight ratio of said nonionic surfactant to the sorbate salt is from 1:2.3990 to 1:109.7646.

The present invention is further directed to a method for inhibiting the growth of mold, preferably *A. niger*, in an aqueous medium by adding: (a) a nonionic surfactant with structure:

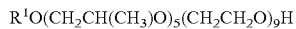
$$R^1O(CH_2CH(CH_3)O)_5(CH_2CH_2O)_9H$$

where $R^1$ is a $C_8$ alkyl group; and (b) a sorbate salt; wherein a weight ratio of said nonionic surfactant to the sorbate salt is from 1:0.1 to 1:0.9143; preferably from 1:0.1 to 1:0.2857 or 1:0.3429 to 1:0.9143.

The present invention is further directed to an aqueous composition comprising from 5 to 40 wt % of a benzoate or sorbate salt and a nonionic surfactant with structure:

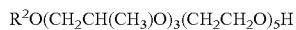
$$R^2O(CH_2CH(CH_3)O)_3(CH_2CH_2O)_5H$$

where $R^2$ is a mixture of $C_8$-$C_{14}$ linear alkyl groups, wherein a weight ratio of said nonionic surfactant to the benzoate or sorbate salt is from 1:0.5 to 1:100. In one preferred embodiment, the benzoate or sorbate salt is a benzoate salt and the weight ratio is from 1:0.5 to 1:100. In another preferred embodiment, the benzoate or sorbate salt is a sorbate salt and the weight ratio is from 1:1 to 1:100. Preferably the composition comprises from 5 to 35 wt % of a benzoate or sorbate salt, preferably from 10 to 30 wt %. Preferably, the composition comprises from 20 to 90 wt % water, preferably from 30 to 80 wt %.

The present invention is further directed to an aqueous composition comprising from 25 to 40 wt % of a sorbate salt and a nonionic surfactant with structure:

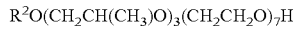
$$R^2O(CH_2CH(CH_3)O)_3(CH_2CH_2O)_7H$$

where $R^2$ is a mixture of $C_8$-$C_{14}$ linear alkyl groups, wherein a weight ratio of said nonionic surfactant to the sorbate salt is from 1:5 to 1:100. Preferably the composition comprises from 28 to 38 wt % of a sorbate salt, preferably from 30 to 35 wt %. Preferably, the composition comprises from 50 to 75 wt % water, preferably from 55 to 72 wt %.

$R^2$ is a mixture of $C_8$-$C_{14}$ linear alkyl groups. Preferably, the $C_8$-$C_{14}$ linear alkyl groups comprise from 50 to 85 wt % $C_8$-$C_{10}$ linear alkyl groups and 15 to 50 wt % $C_{12}$-$C_{14}$ linear alkyl groups, preferably from 60 to 75 wt % $C_8$-$C_{10}$ linear alkyl groups and 25 to 40 wt % $C_{12}$-$C_{14}$ linear alkyl groups, preferably about 70 wt % $C_8$-$C_{10}$ linear alkyl groups and about 30 wt % $C_{12}$-$C_{14}$ linear alkyl groups. Preferably, the linear alkyl groups are derived from seed oil.

Preferably, each of the synergistic microbicidal compositions is substantially free of microbicides other than the nonionic surfactant and the sorbate or benzoate salt, i.e., it has less than 1 wt % of microbicides other than the nonionic surfactant and the sorbate or benzoate salt based on total weight of active ingredients, preferably less than 0.5 wt %, preferably less than 0.2 wt %, preferably less than 0.1 wt %. Preferably, when the nonionic surfactant and the sorbate or benzoate salt are added to an aqueous medium, the medium is substantially free of other microbicides, i.e., it has less than 1 wt % of microbicides other than the nonionic surfactant and the sorbate or benzoate salt based on total weight of active ingredients, preferably less than 0.5 wt %, preferably less than 0.2 wt %, preferably less than 0.1 wt %.

The compositions of this invention may contain other ingredients, e.g., defoamers and emulsifiers. The microbicidal compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions into an aqueous medium subject to microbial attack. Suitable aqueous media are found in, for example: industrial process water; electrocoat deposition systems; cooling towers; air washers; gas scrubbers; mineral slurries; wastewater treatment; ornamental fountains; reverse osmosis filtration; ultra-filtration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; personal care products such as wipes, lotions, sunscreen, conditioners, creams, and other leave-on applications; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

The specific amount of the microbicidal compositions of this invention necessary to inhibit or control the growth of microorganisms in an application will vary. Typically, the amount of the composition of the present invention is sufficient to control the growth of microorganisms if it provides from 1,000 to 30,000 ppm (parts per million) active ingredients of the composition. It is preferred that the active ingredients (i.e., nonionic surfactant and sorbate or benzoate salt) of the composition be present in the medium to be treated in an amount of at least 2,000 ppm, preferably at least 3,000 ppm, preferably at least 4,000 ppm, preferably at least 6,000 ppm, preferably at least 8,000 ppm. It is preferred that the active ingredients of the composition be present in the locus in an amount of no more than 25,000 ppm, preferably no more than 20,000 ppm, preferably no more than 15,000 ppm, preferably no more than 10,000 ppm, preferably no more than 8,000 ppm. In a method of this invention, a composition is treated to inhibit microbial growth by adding, together or separately, the nonionic surfactant and sorbate or benzoate salt, in amounts that would produce the concentrations indicated above.

EXAMPLES

Surfactants and biocides were evaluated for synergy by determining the synergy index (S.I.) of the combination. Synergy index was calculated based on minimum inhibitory concentrations (MIC) of two antimicrobial compounds (A and B) alone and in combinations. The tests organisms were Gram negative bacteria (*Pseudomonas aeruginosa* ATCC #15442), Gram positive bacteria (*Staphylococcus aureus* ATCC #6538), yeast (*Candida albicans* ATCC#10203) and mold (*Aspergillus niger* ATCC#16404). Contact time for the bacteria was 24 and 48 hours, yeast was 48 and 72 hrs, and 3 and 7 days for mold. The test was carried out in 96 well microtiter plates.

Surf. A $R^1O(CH_2CH(CH_3)O)_5(CH_2CH_2O)_9H$, where $R^1$ is 2-ethylhexyl

Surf. D $R^2O(CH_2CH(CH_3)O)_3(CH_2CH_2O)_5H$

Surf. E $R^2O(CH_2CH(CH_3)O)_3(CH_2CH_2O)_7H$

In Surf. D and Surf. E, $R^2$ is a mixture of $C_8$-$C_{14}$ linear alkyl groups (70% $C_8$-$C_{10}$ linear alkyl and 30% $C_{12}$-$C_{14}$ linear alkyl)

Inoculums Used
Inoculum Size of organisms (CFU/ml)

| Surfactants | Staphylococcus aureus ATCC# 6538 | Pseudomonas aeruginosa ATCC# 15442 | Aspergillus niger ATCC# 16404 | Candida albicans ATCC# 10203 |
|---|---|---|---|---|
| Surf. A | 1.156E+06 | 8.134E+07 | 1.156E+06 | 1.156+06 |
| Surf. D | 1.808E+05 | 1.156E+08 | 1.156E+06 | 5.726E+05 |
| Surf. E | 1.808E+06 | 5.727E+07 | 5.726E+05 | 1.808E+06 |

TABLE 4

Media Used
Media Used for testing

| Staphylococcus aureus ATCC# 6538 | Pseudomonas aeruginosa ATCC# 15442 | Aspergillus niger ATCC# 16404 | Candida albicans ATCC# 10203 |
|---|---|---|---|
| 10% Tryptic soy broth | 10% Tryptic soy broth | Potato dextrose broth | Potato dextrose broth |

The pH of the Triptic soy broth was 7.3 and the Potato dextrose broth was 5.1

The test results for demonstration of synergy of the MIC combinations are shown in the tables below. Each table shows the results for combinations of two components against the microorganisms tested with incubation times; the end-point activity in ppm measured by the MIC for compound A alone (CA), for component B alone (CB), and the mixture (Ca) and (Cb); the calculated SI value; and the range of synergistic ratios for each combination tested. SI is calculated as follows:

$$Ca/CA + Cb/CB = \text{Synergy Index (``SI'')}$$

Wherein:
  CA=concentration of compound A in ppm, acting alone, which produced an end point (MIC of Compound A).
  Ca=concentration of compound A in ppm, in the mixture, which produced an end point.
  CB=concentration of compound B in ppm, acting alone, which produced an end point (MIC of Compound B).
  Cb=concentration of compound B in ppm, in the mixture, which produced an end point.

When the sum of Ca/CA and Cb/CB is greater than one, antagonism is indicated. When the sum is equal to one, additivity is indicated, and when less than one, synergism is demonstrated.

The ratio ranges at which sorbate, benzoate and the surfactants were tested are as summarized in the following tables:

Sodium Benzoate with Surf. A

| Organism | ATCC# | From | To | Ratio Range |
|---|---|---|---|---|
| Staphylococcus aureus | 6538 | 0.2:20,000 | 1,000:218.75 | 1:0.00001-1:4.5714 |
| Aspergillus niger | 16404 | 0.2:20,000 | 1,000:218.75 | 1:0.00001-1:4.5714 |
| Candida albicans | 10203 | 0.2:20,000 | 1,000:218.75 | 1:0.00001-1:4.5714 |
| Pseudomonas aeruginosa | 15442 | 0.2:20,000 | 1,000:218.75 | 1:0.00001-1:4.5714 |

Sodium Benzoate with Surf. E

| Organism | ATCC# | From | To | Ratio Range |
|---|---|---|---|---|
| Staphylococcus aureus | 6538 | 6.0:20,000 | 30,000:218.75 | 1:0.0003-1:137.143 |
| Aspergillus niger | 16404 | 0.2:20,000 | 1,000:218.75 | 1:0.00001-1:4.5714 |
| Candida albicans | 10203 | 0.2:20,000 | 1,000:218.75 | 1:0.00001-1:4.5714 |
| Pseudomonas aeruginosa | 15442 | 6.0:20,000 | 30,000:218.75 | 1:0.0003-1:137.143 |

Sodium Benzoate with Surf. D

| Organism | ATCC# | From | To | Ratio Range |
|---|---|---|---|---|
| Staphylococcus aureus | 6538 | 6.0:20,000 | 30,000:218.75 | 1:0.0003-1:137.143 |
| Aspergillus niger | 16404 | 6.0:20,000 | 30,000:218.75 | 1:0.0003-1:137.143 |
| Candida albicans | 10203 | 6.0:20,000 | 30,000:218.75 | 1:0.0003-1:137.143 |
| Pseudomonas aeruginosa | 15442 | 6.0:20,000 | 30,000:218.75 | 1:0.0003-1:137.143 |

Potassium Sorbate with Surf. A

| Organism | ATCC# | From | To | Ratio Range |
|---|---|---|---|---|
| Staphylococcus aureus | 6538 | 0.2:20,000 | 1,000:218.75 | 1:0.00001-1:4.5714 |
| Aspergillus niger | 16404 | 0.2:20,000 | 1,000:218.75 | 1:0.00001-1:4.5714 |
| Candida albicans | 10203 | 0.2:20,000 | 1,000:218.75 | 1:0.00001-1:4.5714 |
| Pseudomonas aeruginosa | 15442 | 0.2:20,000 | 1,000:218.75 | 1:0.00001-1:4.5714 |

Potassium Sorbate with Surf. E

| Organism | ATCC# | From | To | Ratio Range |
|---|---|---|---|---|
| Staphylococcus aureus | 6538 | 6.0:20,000 | 30,000:218.75 | 1:0.0003-1:137.143 |
| Aspergillus niger | 16404 | 0.2:20,000 | 1,000:218.75 | 1:0.00001-1:4.5714 |
| Candida albicans | 10203 | 0.2:20,000 | 1,000:218.75 | 1:0.00001-1:4.5714 |
| Pseudomonas aeruginosa | 15442 | 6.0:20,000 | 30,000:218.75 | 1:0.0003-1:137.143 |

| Potassium Sorbate with Surf. D | | | | |
|---|---|---|---|---|
| Organism | ATCC# | From | To | Ratio Range |
| Staphylococcus aureus | 6538 | 6.0:20,000 | 30,000:218.75 | 1:0.0003-1:137.143 |
| Aspergillus niger | 16404 | 6.0:20,000 | 30,000:218.75 | 1:0.0003-1:137.143 |
| Candida albicans | 10203 | 6.0:20,000 | 30,000:218.75 | 1:0.0003-1:137.143 |
| Pseudomonas aeruginosa | 15442 | 6.0:20,000 | 30,000:218.75 | 1:0.0003-1:137.143 |

| A: Surf. A | | |
|---|---|---|
| B: Sodium Benzoate | | |
| A. niger | ATCC# 16404 | No Synergy |
| C. albicans | ATCC# 10203 | No Synergy |
| Ps. aeruginosa | ATCC# 15442 | No Synergy |
| S. aureus | ATCC# 6538 | No Synergy |

A: Surf. D
B: Sodium Benzoate
Media: PDB
Inoculum size: 1.156E+06

| PPM AI MIC Values (3rd day) | | | | | | |
|---|---|---|---|---|---|---|
| Test | Alone | | Combination | | | Ratio |
| Organism | CA | CB | Ca | Cb | S.I. | (Ca:Cb) |
| A. niger ATCC#16404 | 20000 | 5998 | 10000 | 2401 | 0.90 | 1:0.2401 |
| | 20000 | 5998 | 10000 | 1801 | 0.80 | 1:0.1801 |
| | 20000 | 5998 | 10000 | 1499 | 0.75 | 1:0.1499 |
| | 20000 | 5998 | 10000 | 1200 | 0.70 | 1:0.1200 |
| | 20000 | 5998 | 5000 | 3000 | 0.75 | 1:0.6000 |
| | 20000 | 5998 | 5000 | 2401 | 0.65 | 1:0.4802 |
| | 20000 | 5998 | 5000 | 1801 | 0.55 | 1:0.3602 |
| | 20000 | 5998 | 5000 | 1499 | 0.50 | 1:0.2998 |
| | 20000 | 5998 | 5000 | 1200 | 0.45 | 1:0.2400 |
| | 20000 | 5998 | 2500 | 3000 | 0.63 | 1:1.2000 |
| | 20000 | 5998 | 2500 | 2401 | 0.53 | 1:0.9604 |
| | 20000 | 5998 | 2500 | 1801 | 0.43 | 1:0.7204 |
| | 20000 | 5998 | 2500 | 1499 | 0.37 | 1:0.5996 |
| | 20000 | 5998 | 2500 | 1200 | 0.33 | 1:0.4800 |
| | 20000 | 5998 | 1750 | 3000 | 0.59 | 1:1.7143 |
| | 20000 | 5998 | 1750 | 2401 | 0.49 | 1:1.3720 |
| | 20000 | 5998 | 1750 | 1801 | 0.39 | 1:1.0291 |
| | 20000 | 5998 | 1750 | 1499 | 0.34 | 1:0.8566 |
| | 20000 | 5998 | 437.5 | 3000 | 0.52 | 1:6.8571 |
| | 20000 | 5998 | 437.5 | 2401 | 0.42 | 1:5.4880 |
| | 20000 | 5998 | 437.5 | 1801 | 0.32 | 1:4.1166 |
| | 20000 | 5998 | 437.5 | 1499 | 0.27 | 1:3.4263 |
| | 20000 | 5998 | 218.75 | 3000 | 0.51 | 1:13.7143 |
| | 20000 | 5998 | 218.75 | 2401 | 0.41 | 1:10.9760 |
| | 20000 | 5998 | 218.75 | 1801 | 0.31 | 1:8.2331 |
| | 20000 | 5998 | 218.75 | 1499 | 0.26 | 1:6.8526 |

A: Surf. D
B: Sodium Benzoate
Media: PDB
Inoculum size: 5.726E+05 CFU/ml

| PPM AI MIC Values (48 hrs) | | | | | | |
|---|---|---|---|---|---|---|
| Test | Alone | | Combination | | | Ratio |
| Organism | CA | CB | Ca | Cb | S.I. | (Ca:Cb) |
| C. albicans ATCC#10203 | 20000 | 1200 | 2500 | 899 | 0.87 | 1:0.3596 |
| | 20000 | 1200 | 1750 | 600 | 0.59 | 1:0.3429 |
| | 20000 | 1200 | 1750 | 899 | 0.84 | 1:0.5137 |

| A: Surf. D | | |
|---|---|---|
| B: Sodium Benzoate | | |
| Ps. aeruginosa | ATCC# 15442 | No Synergy |

A: Surf. D
B: Sodium Benzoate
Media: 1/10 TSB
Inoculum size: 1.808E+05

| PPM AI MIC Values (24 hrs) | | | | | | |
|---|---|---|---|---|---|---|
| Test | Alone | | Combination | | | Ratio |
| Organism | CA | CB | Ca | Cb | S.I. | (Ca:Cb) |
| S. aureus ATCC# 6538 | 20000 | 30000 | 5000 | 14991 | 0.75 | 1:2.9982 |
| | 20000 | 30000 | 1750 | 14991 | 0.59 | 1:8.5663 |
| | 20000 | 30000 | 1750 | 24011 | 0.89 | 1:13.7206 |
| | 20000 | 30000 | 1750 | 18005 | 0.69 | 1:10.2886 |
| | 20000 | 30000 | 875 | 24011 | 0.84 | 1:27.4411 |
| | 20000 | 30000 | 875 | 18005 | 0.64 | 1:20.5771 |
| | 20000 | 30000 | 875 | 14991 | 0.54 | 1:17.1326 |
| | 20000 | 30000 | 437.5 | 24011 | 0.82 | 1:54.8823 |
| | 20000 | 30000 | 437.5 | 18005 | 0.62 | 1:41.1543 |
| | 20000 | 30000 | 437.5 | 14991 | 0.52 | 1:34.2651 |
| | 20000 | 30000 | 218.75 | 24011 | 0.81 | 1:109.7646 |
| | 20000 | 30000 | 218.75 | 18005 | 0.61 | 1:82.3086 |
| | 20000 | 30000 | 218.75 | 14991 | 0.51 | 1:68.5303 |

| A: Surf. E | | |
|---|---|---|
| B: Sodium Benzoate | | |
| A. niger | ATCC# 16404 | No Synergy |
| C. albicans | ATCC# 10203 | No Synergy |

A: Surf. E
B: Sodium Benzoate
Media: 1/10TSB
Inoculum size: 5.727E+07 CFU/ml

| PPM AI MIC Values (48 hrs) | | | | | | |
|---|---|---|---|---|---|---|
| Test | Alone | | Combination | | | Ratio |
| Organism | CA | CB | Ca | Cb | S.I. | (Ca:Cb) |
| Ps. aeruginosa ATCC#15442 | 20000 | 14991 | 437.5 | 11995 | 0.82 | 1:27.4171 |
| | 20000 | 14991 | 218.75 | 11995 | 0.81 | 1:54.8343 |

A: Surf. E
B: Sodium benzoate
Media: 1/10TSB
Inoculum size: 1.808E+06 CFU/ml

| PPM AI MIC Values (24 hrs) | | | | | | |
|---|---|---|---|---|---|---|
| Test | Alone | | Combination | | Ratio | |
| Organism | CA | CB | Ca | Cb | S.I. | (Ca:Cb) |
| S. aureus | 20000 | 30000 | 5000 | 18005 | 0.85 | 1:3.6010 |
| ATCC# 6538 | 20000 | 30000 | 2500 | 24011 | 0.93 | 1:9.6044 |
| | 20000 | 30000 | 1750 | 24011 | 0.89 | 1:13.7206 |
| | 20000 | 30000 | 1750 | 18005 | 0.69 | 1:10.2886 |
| | 20000 | 30000 | 875 | 24011 | 0.84 | 1:27.4411 |
| | 20000 | 30000 | 437.5 | 24011 | 0.82 | 1:54.8823 |
| | 20000 | 30000 | 437.5 | 18005 | 0.62 | 1:41.1543 |
| | 20000 | 30000 | 218.75 | 24011 | 0.81 | 1:109.7646 |

A: Surf. A
B: Potassium Sorbate
Media: PDB
Inoculum size: 1.156E+06 CFU/ml

| PPM AI MIC Values (3rd day) | | | | | | |
|---|---|---|---|---|---|---|
| Test | Alone | | Combination | | Ratio | |
| Organism | CA | CB | Ca | Cb | S.I. | (Ca:Cb) |
| A. niger | 20000 | 1000 | 5000 | 500 | 0.75 | 1:0.1000 |
| ATCC#16404 | 20000 | 1000 | 5000 | 600 | 0.85 | 1:0.1200 |
| | 20000 | 1000 | 2500 | 500 | 0.63 | 1:0.2000 |
| | 20000 | 1000 | 2500 | 600 | 0.73 | 1:0.2400 |
| | 20000 | 1000 | 2500 | 800 | 0.93 | 1:0.3200 |
| | 20000 | 1000 | 1750 | 500 | 0.59 | 1:0.2857 |
| | 20000 | 1000 | 1750 | 600 | 0.69 | 1:0.3429 |
| | 20000 | 1000 | 1750 | 800 | 0.89 | 1:0.4571 |
| | 20000 | 1000 | 875 | 500 | 0.54 | 1:0.5714 |
| | 20000 | 1000 | 875 | 600 | 0.64 | 1:0.6857 |
| | 20000 | 1000 | 875 | 800 | 0.84 | 1:0.9143 |

A: Surf. A
B: Potassium Sorbate
Media: PDB
Inoculum size: 1.156E+06 CFU/ml

| PPM AI MIC Values (48 hrs) | | | | | | |
|---|---|---|---|---|---|---|
| Test | Alone | | Combination | | Ratio | |
| Organism | CA | CB | Ca | Cb | S.I. | (Ca:Cb) |
| C. albicans ATCC#10203 | 20000 | 800 | 218.75 | 600 | 0.76 | 1:2.7429 |

| A: Surf. A B: Potassium Sorbate | | |
|---|---|---|
| Ps. aeruginosa | ATCC# 15442 | No Synergy |
| S. aureus | ATCC# 6538 | No Synergy |

A: Surf. D
B: Potassium Sorbate
Media: PDB
Inoculum size: 1.156E+06

| PPM AI MIC Values (3rd day) | | | | | | |
|---|---|---|---|---|---|---|
| Test | Alone | | Combination | | Ratio | |
| Organism | CA | CB | Ca | Cb | S.I. | (Ca:Cb) |
| A. niger | 20000 | 5998 | 10000 | 2401 | 0.90 | 1:0.2401 |
| ATCC#16404 | 20000 | 5998 | 10000 | 1801 | 0.80 | 1:0.1801 |
| | 20000 | 5998 | 10000 | 1499 | 0.75 | 1:0.1499 |
| | 20000 | 5998 | 10000 | 1200 | 0.70 | 1:0.1200 |
| | 20000 | 5998 | 5000 | 3000 | 0.75 | 1:0.6000 |
| | 20000 | 5998 | 5000 | 2401 | 0.65 | 1:0.4802 |
| | 20000 | 5998 | 5000 | 1801 | 0.55 | 1:0.3602 |
| | 20000 | 5998 | 5000 | 1499 | 0.50 | 1:0.2998 |
| | 20000 | 5998 | 5000 | 1200 | 0.45 | 1:0.2400 |
| | 20000 | 5998 | 2500 | 3000 | 0.63 | 1:1.2000 |
| | 20000 | 5998 | 2500 | 2401 | 0.53 | 1:0.9604 |
| | 20000 | 5998 | 2500 | 1801 | 0.43 | 1:0.7204 |
| | 20000 | 5998 | 2500 | 1499 | 0.37 | 1:0.5996 |
| | 20000 | 5998 | 2500 | 1200 | 0.33 | 1:0.4800 |
| | 20000 | 5998 | 1750 | 3000 | 0.59 | 1:1.7143 |
| | 20000 | 5998 | 1750 | 2401 | 0.49 | 1:1.3720 |
| | 20000 | 5998 | 1750 | 1801 | 0.39 | 1:1.0291 |
| | 20000 | 5998 | 1750 | 1499 | 0.34 | 1:0.8566 |
| | 20000 | 5998 | 437.5 | 3000 | 0.52 | 1:6.8571 |
| | 20000 | 5998 | 437.5 | 2401 | 0.42 | 1:5.4880 |
| | 20000 | 5998 | 437.5 | 1801 | 0.32 | 1:4.1166 |
| | 20000 | 5998 | 437.5 | 1499 | 0.27 | 1:3.4263 |
| | 20000 | 5998 | 218.75 | 3000 | 0.51 | 1:13.7143 |
| | 20000 | 5998 | 218.75 | 2401 | 0.41 | 1:10.9760 |
| | 20000 | 5998 | 218.75 | 1801 | 0.31 | 1:8.2331 |
| | 20000 | 5998 | 218.75 | 1499 | 0.26 | 1:6.8526 |

A: Surf. D
B: Potassium Sorbate
Media: PDB
Inoculum size: 5.726E+05 CFU/ml

| PPM AI MIC Values (48 hrs) | | | | | | |
|---|---|---|---|---|---|---|
| Test | Alone | | Combination | | Ratio | |
| Organism | CA | CB | Ca | Cb | S.I. | (Ca:Cb) |
| C. albicans | 20000 | 1200 | 2500 | 899 | 0.87 | 1:0.3596 |
| ATCC#10203 | 20000 | 1200 | 1750 | 600 | 0.59 | 1:0.3429 |
| | 20000 | 1200 | 1750 | 899 | 0.84 | 1:0.5137 |

| A: Surf. D B: Potassium Sorbate | | |
|---|---|---|
| Ps. aeruginosa | ATCC# 15442 | No Synergy |

A: Surf. D
B: Potassium Sorbate
Media: 1/10 TSB
Inoculum size: 1.808E+05

| PPM AI MIC Values (24 hrs) | | | | | | |
|---|---|---|---|---|---|---|
| Test | Alone | | Combination | | Ratio | |
| Organism | CA | CB | Ca | Cb | S.I. | (Ca:Cb) |
| S. aureus | 20000 | 30000 | 5000 | 14991 | 0.75 | 1:2.9982 |
| ATCC# 6538 | 20000 | 30000 | 1750 | 14991 | 0.59 | 1:8.5663 |
| | 20000 | 30000 | 1750 | 24011 | 0.89 | 1:13.7206 |
| | 20000 | 30000 | 1750 | 18005 | 0.69 | 1:10.2886 |
| | 20000 | 30000 | 875 | 24011 | 0.84 | 1:27.4411 |
| | 20000 | 30000 | 875 | 18005 | 0.64 | 1:20.5771 |
| | 20000 | 30000 | 875 | 14991 | 0.54 | 1:17.1326 |

| Test Organism | Alone CA | Alone CB | Combination Ca | Combination Cb | S.I. | Ratio (Ca:Cb) |
|---|---|---|---|---|---|---|
| | 20000 | 30000 | 437.5 | 24011 | 0.82 | 1:54.8823 |
| | 20000 | 30000 | 437.5 | 18005 | 0.62 | 1:41.1543 |
| | 20000 | 30000 | 437.5 | 14991 | 0.52 | 1:34.2651 |
| | 20000 | 30000 | 218.75 | 24011 | 0.81 | 1:109.7646 |
| | 20000 | 30000 | 218.75 | 18005 | 0.61 | 1:82.3086 |
| | 20000 | 30000 | 218.75 | 14991 | 0.51 | 1:68.5303 |

A: Surf. E
B: Potassium Sorbate
Media: PDB
Inoculum size: 1.156E+06 CFU/ml

PPM AI MIC Values (3rd day)

| Test Organism | Alone CA | Alone CB | Combination Ca | Combination Cb | S.I. | Ratio (Ca:Cb) |
|---|---|---|---|---|---|---|
| A. niger ATCC#16404 | 20000 | 1000 | 5000 | 600 | 0.85 | 1:0.1200 |
| | 20000 | 1000 | 2500 | 800 | 0.93 | 1:0.3200 |

A: Surf. E
B: Potassium Sorbate
Media: PDB
Inoculum size: 1.808E+06 CFU/ml

PPM AI MIC Values (48 hrs)

| Test Organism | Alone CA | Alone CB | Combination Ca | Combination Cb | S.I. | Ratio (Ca:Cb) |
|---|---|---|---|---|---|---|
| C. albicans ATCC#10203 | 20000 | 600 | 5000 | 300 | 0.75 | 1:0.0600 |
| | 20000 | 600 | 5000 | 400 | 0.92 | 1:0.0800 |
| | 20000 | 600 | 2500 | 400 | 0.79 | 1:0.1600 |
| | 20000 | 600 | 2500 | 500 | 0.96 | 1:0.2000 |
| | 20000 | 600 | 1750 | 400 | 0.75 | 1:0.2286 |
| | 20000 | 600 | 1750 | 500 | 0.92 | 1:0.2857 |
| | 20000 | 600 | 875 | 500 | 0.88 | 1:0.5714 |

A: Surf. E
B: Potassium Sorbate
Media: 1/10TSB
Inoculum size: 5.727E+07 CFU/ml

PPM AI MIC Values (24 hrs)

| Test Organism | Alone CA | Alone CB | Combination Ca | Combination Cb | S.I. | Ratio (Ca:Cb) |
|---|---|---|---|---|---|---|
| Ps. aeruginosa ATCC#15442 | 20000 | 14991 | 875 | 11995 | 0.84 | 1:13.7086 |
| | 20000 | 14991 | 437.5 | 11995 | 0.82 | 1:27.4171 |

A: Surf. E
B: Potassium Sorbate
Media: 1/10TSB
Inoculum size: 1.808E+06 CFU/ml

PPM AI MIC Values (24 hrs)

| Test Organism | Alone CA | Alone CB | Combination Ca | Combination Cb | S.I. | Ratio (Ca:Cb) |
|---|---|---|---|---|---|---|
| S. aureus ATCC# 6538 | 20000 | 30000 | 5000 | 11995 | 0.65 | 1:2.3990 |
| | 20000 | 30000 | 5000 | 14991 | 0.75 | 1:2.9982 |
| | 20000 | 30000 | 5000 | 18005 | 0.85 | 1:3.6010 |
| | 20000 | 30000 | 2500 | 11995 | 0.52 | 1:4.7980 |
| | 20000 | 30000 | 2500 | 14991 | 0.62 | 1:5.9964 |
| | 20000 | 30000 | 2500 | 18005 | 0.73 | 1:7.2020 |
| | 20000 | 30000 | 2500 | 24011 | 0.93 | 1:9.6044 |
| | 20000 | 30000 | 1750 | 11995 | 0.49 | 1:6.8543 |
| | 20000 | 30000 | 1750 | 14991 | 0.59 | 1:8.5663 |
| | 20000 | 30000 | 1750 | 18005 | 0.69 | 1:10.2886 |
| | 20000 | 30000 | 1750 | 24011 | 0.89 | 1:13.7206 |
| | 20000 | 30000 | 875 | 11995 | 0.44 | 1:13.7086 |
| | 20000 | 30000 | 875 | 14991 | 0.54 | 1:17.1326 |
| | 20000 | 30000 | 875 | 18005 | 0.64 | 1:20.5771 |
| | 20000 | 30000 | 875 | 24011 | 0.84 | 1:27.4411 |
| | 20000 | 30000 | 437.5 | 14991 | 0.52 | 1:34.2651 |
| | 20000 | 30000 | 437.5 | 18005 | 0.62 | 1:41.1543 |
| | 20000 | 30000 | 437.5 | 24011 | 0.82 | 1:54.8823 |
| | 20000 | 30000 | 218.75 | 14991 | 0.51 | 1:68.5303 |
| | 20000 | 30000 | 218.75 | 18005 | 0.61 | 1:82.3086 |
| | 20000 | 30000 | 218.75 | 24011 | 0.81 | 1:109.7646 |

The following biocides had no synergy against any organism tested when paired with the following surfactants:

Surf. A
Sodium Benzoate, TRIS NITRO
Surf. E
DMDMH
Surf. D
CS-1246, OPP, DMDMH

In the following combinations, the ratio of surfactant to biocide where synergy was observed were not commercially relevant, i.e., a ratio of 1:0.2 or greater (less biocide relative to surfactant). At these ratios, the biocide levels in a formulated product would be too low to be practical:

Surf. A
DIDAC, IPBC
Surf. E
CMIT/MIT, IPBC, OIT, TTPC, WSCP
Surf. D
CMIT/MIT, OIT, DIDAC
(MBIT, IPBC, WSCP were synergistic only at 1:0.05 or worse except for one data point)

Stability Testing

A solution of sodium benzoate or potassium sorbate in water was made and diluted with surfactant to give the desired ratios of biocide to surfactant. Additional water was added as needed to give the indicate wt % solutions. The samples were split into three vials. One vial was stored at room temperature, one was stored at 40° C. and one was stored at 50° C. Samples were evaluated after a week to determine stability. Samples that were cloudy or highly discolored were determined to be unstable. In the data tables, a dash indicates that the formulation was stable.

| Stability Data-10% Sodium benzoate in combination with Surfactants- Day 1 | | | | |
|---|---|---|---|---|
| | Surfactant: | Temperature | | |
| Surfactant | Sodium benzoate | Room Temperature | 40° C. | 50° C. |
| Surf. D | 1:0.5 | — | — | — |
| | 1:27 | — | — | — |
| | 1:100 | — | — | — |
| Surf. E | 1:27 | — | — | — |
| | 1:10 | — | — | — |
| Surf. B | 1:27 | — | — | — |
| POLYSORBATE 20 | 1:10 | — | — | — |
| | 1:27 | — | — | — |
| | 1:100 | — | — | — |
| Disodium cocoamphodiacetate | 1:10 | — | — | — |
| | 1:27 | — | — | — |
| | 1:100 | — | — | — |
| TERGITOL L-62 | 1:10 | — | — | Cloudy |
| | 1:27 | — | Slightly cloudy | Cloudy |
| | 1:100 | — | Slightly cloudy | Slightly cloudy |
| TERGITOL 81 | 1:10 | Slightly cloudy | Slightly cloudy | Cloudy |
| | 1:27 | Slightly cloudy | Slightly cloudy | Cloudy |
| | 1:100 | — | — | Slightly cloudy |
| TERGITOL 15-S-7 | 1:10 | — | — | — |
| | 1:27 | — | — | — |
| | 1:100 | — | — | — |

* Surf. B is $R^1O(CH_2CH(CH_3)O)_5(CH_2CH_2O)_6H$, where $R^1$ is 2-ethylhexyl

| Stability Data-10% Sodium benzoate in combination with Surfactants- Day 2 | | | | |
|---|---|---|---|---|
| | Surfactant: | Temperature | | |
| Surfactant | Sodium benzoate | Room Temperature | 40° C. | 50° C. |
| Surf. D | 1:0.5 | — | — | — |
| | 1:27 | — | — | — |
| | 1:100 | — | — | — |
| Surf. E | 1:27 | — | — | — |
| | 1:10 | — | — | — |
| Surf. B | 1:27 | — | — | — |
| POLYSORBATE 20 | 1:10 | — | — | — |
| | 1:27 | — | — | — |
| | 1:100 | — | — | — |
| Disodium cocoamphodiacetate | 1:10 | — | — | — |
| | 1:27 | — | — | — |
| | 1:100 | — | — | — |
| TERGITOL L-62 | 1:10 | — | — | Cloudy |
| | 1:27 | — | Slightly cloudy | Cloudy |
| | 1:100 | — | Slightly cloudy | Slightly cloudy |
| TERGITOL 81 | 1:10 | Slightly cloudy | Slightly cloudy | Cloudy + while precipitate |
| | 1:27 | Slightly cloudy | Slightly cloudy | Cloudy + white precipitate |
| | 1:100 | — | — | Slightly cloudy + white precipitate |
| TERGITOL 15-S-7 | 1:10 | — | — | — |
| | 1:27 | — | — | — |
| | 1:100 | — | — | — |

| Stability Data-10% Sodium benzoate in combination with Surfactants- Day 7 | | | | |
|---|---|---|---|---|
| | Surfactant: | Temperature | | |
| Surfactant | Sodium benzoate | Room Temperature | 40° C. | 50° C. |
| Surf. D | 1:0.5 | — | — | — |
| | 1:27 | — | — | — |
| | 1:100 | — | — | — |
| Surf. E | 1:27 | — | — | — |
| | 1:10 | — | — | — |
| Surf. B | 1:27 | — | — | — |
| POLYSORBATE 20 | 1:10 | — | — | — |
| | 1:27 | — | — | — |
| | 1:100 | — | — | — |
| Disodium cocoamphodiacetate | 1:10 | — | — | — |
| | 1:27 | — | — | — |
| | 1:100 | — | — | — |
| TERGITOL L-62 | 1:10 | — | — | Cloudy |
| | 1:27 | — | Slightly Cloudy | Cloudy |
| | 1:100 | — | Slightly cloudy | Slightly cloudy |
| TERGITOL 81 | 1:10 | Slightly cloudy | Cloudy | Cloudy |
| | 1:27 | Slightly cloudy | Cloudy | Cloudy |
| | 1:100 | — | Slightly cloudy | Slightly cloudy |
| TERGITOL 15-S-7 | 1:10 | — | — | — |
| | 1:27 | — | — | — |
| | 1:100 | — | — | — |

| Stability Data-30% Sodium benzoate in combination with Surfactants- Day 1 | | | | |
|---|---|---|---|---|
| | Surfactant: | Temperature | | |
| Surfactant | Sodium benzoate | Room Temperature | 40° C. | 50° C. |
| Surf. D | 1:0.5 | — | — | — |
| | 1:27 | — | — | — |
| | 1:100 | — | — | — |
| Surf. E | 1:27 | — | — | — |
| | 1:10 | — | — | — |
| Surf. B | 1:27 | — | — | — |
| POLYSORBATE 20 | 1:10 | — | — | — |
| | 1:27 | — | — | — |
| | 1:100 | — | — | — |
| Disodium cocoamphodiacetate | 1:10 | — | — | — |
| | 1:27 | — | — | — |
| | 1:100 | — | — | — |
| TERGITOL L-61 | 1:10 | — | — | — |
| | 1:27 | — | — | — |
| | 1:100 | — | — | — |
| TERGITOL 81 | 1:10 | — | — | — |
| | 1:27 | — | — | — |
| | 1:100 | — | — | — |
| TERGITOL 15-S-7 | 1:10 | — | — | — |
| | 1:27 | — | — | — |
| | 1:100 | — | — | — |

| Stability Data-30% Sodium benzoate in combination with Surfactants- Day 2 | | | | |
|---|---|---|---|---|
| | Surfactant: | Temperature | | |
| Surfactant | Sodium benzoate | Room Temperature | 40° C. | 50° C. |
| Surf. D | 1:0.5 | — | — | — |
| | 1:27 | — | — | — |
| | 1:100 | — | — | — |
| Surf. E | 1:27 | — | — | — |
| | 1:10 | — | — | — |
| Surf. B | 1:27 | — | — | — |
| POLYSORBATE 20 | 1:10 | — | — | — |
| | 1:27 | — | — | — |
| | 1:100 | — | — | — |
| Disodium cocoamphodiacetate | 1:10 | — | — | — |
| | 1:27 | — | — | — |
| | 1:100 | — | — | — |
| Tergitol L-61 | 1:10 | — | — | — |
| | 1:27 | — | — | — |
| | 1:100 | — | — | — |
| TERGITOL 81 | 1:10 | — | — | — |
| | 1:27 | — | — | — |
| | 1:100 | — | — | — |
| TERGITOL 15-S-7 | 1:10 | — | — | — |
| | 1:27 | — | — | — |
| | 1:100 | — | — | — |

| Stability Data-30% Sodium benzoate in combination with Surfactants- Day 7 | | | | |
|---|---|---|---|---|
| | Surfactant: | Temperature | | |
| Surfactant | Sodium benzoate | Room Temperature | 40° C. | 50° C. |
| Surf. D | 1:0.5 | — | — | — |
| | 1:27 | — | — | — |
| | 1:100 | — | — | — |
| Surf. E | 1:27 | — | — | — |
| | 1:10 | — | — | — |
| Surf. B | 1:27 | — | — | — |
| POLYSORBATE 20 | 1:10 | — | — | — |
| | 1:27 | — | — | — |
| | 1:100 | — | — | — |
| Disodium cocoamphodiacetate | 1:10 | — | — | — |
| | 1:27 | — | — | — |
| | 1:100 | — | — | — |
| TERGITOL L-61 | 1:10 | — | — | White solid |
| | 1:27 | — | — | — |
| | 1:100 | — | — | — |
| TERGITOL 81 | 1:10 | — | — | White precipitate |
| | 1:27 | — | — | — |
| | 1:100 | — | — | — |
| TERGITOL 15-S-7 | 1:10 | — | — | — |
| | 1:27 | — | — | — |
| | 1:100 | — | — | — |

| Stability Data-33% Potassium sorbate in combination with Surfactants- Day 3 | | | | |
|---|---|---|---|---|
| | Surfactant: | Temperature | | |
| Surfactant | Sodium benzoate | Room Temperature | 40° C. | 50° C. |
| Surf. D | 1:1 | — | — | — |
| | 1:27 | — | — | — |
| | 1:68 | — | — | — |
| | 1:100 | — | — | — |
| Surf. E | 1:5 | — | — | — |
| | 1:27 | — | — | — |
| | 1:68 | — | — | — |
| | 1:100 | — | — | — |
| Surf. A | 1:0.5 | — | — | — |
| | 1:27 | — | — | — |
| Surf. B | 1:0.5 | — | — | — |
| | 1:27 | — | — | — |
| POLYSORBATE 20 | 1:1 | — | — | — |
| | 1:27 | — | — | — |
| | 1:68 | — | — | — |
| | 1:100 | — | — | — |
| Disodium cocoamphodiacetate | 1:1 | White precipitate | White precipitate | White precipitate |
| | 1:27 | — | — | — |
| | 1:68 | — | — | — |
| | 1:100 | — | — | — |
| TERGITOL L-62 | 1:1 | — | — | — |
| | 1:27 | — | — | — |
| | 1:68 | — | — | — |
| | 1:100 | — | — | — |
| TERGITOL 81 | 1:1 | — | — | — |
| | 1:27 | — | Cloudy | — |
| | 1:68 | — | Cloudy | Cloudy |
| | 1:100 | — | — | Cloudy |
| TERGITOL 15-S-7 | 1:1 | — | — | — |
| | 1:27 | — | — | — |
| | 1:68 | — | — | — |
| | 1:100 | — | — | — |

Note:
All Room Temperature and 40° C. samples were a light yellow color unless noted, and all 50° C. samples were dark yellow unless noted.

| Stability Data-33% Potassium sorbate in combination with Surfactants-Day 7 | | | | |
|---|---|---|---|---|
| | Surfactant: | Temperature | | |
| Surfactant | Sodium benzoate | Room Temperature | 40° C. | 50° C. |
| Surf. D | 1:1 | — | — | Brown solid |
| | 1:27 | — | — | — |
| | 1:68 | — | — | — |
| | 1:100 | — | — | — |
| Surf. E | 1:5 | — | — | — |
| | 1:27 | — | — | — |
| | 1:68 | — | — | — |
| | 1:100 | — | — | — |
| Surf. A | 1:0.5 | — | — | — |
| | 1:27 | — | — | — |
| Surf. B | 1:0.5 | — | — | — |
| | 1:27 | — | — | — |
| POLYSORBATE 20 | 1:1 | — | Amber | — |
| | 1:27 | — | — | — |
| | 1:68 | — | — | — |
| | 1:100 | — | — | — |
| Disodium cocoamphodiacetate | 1:1 | White precipitate | White precipitate | Brown solid |
| | 1:27 | — | Amber | — |
| | 1:68 | — | Amber | — |
| | 1:100 | — | Amber | — |
| TERGITOL L-62 | 1:1 | — | — | Brown solid |
| | 1:27 | — | — | — |
| | 1:68 | — | — | — |
| | 1:100 | — | — | — |

-continued

| Stability Data-33% Potassium sorbate in combination with Surfactants-Day 7 | | | | |
|---|---|---|---|---|
| | Surfactant: | Temperature | | |
| Surfactant | Sodium benzoate | Room Temperature | 40° C. | 50° C. |
| Tergitol 81 | 1:1 | — | — | Brown solid |
| | 1:27 | — | cloudy | — |
| | 1:68 | — | — | — |
| | 1:100 | — | — | — |
| Tergitol 15-S-7 | 1:1 | — | — | — |
| | 1:27 | — | — | — |
| | 1:68 | — | — | — |
| | 1:100 | — | — | — |

Note:
All Room Temperature were a light yellow color unless noted, all 40° C. samples were dark yellow unless noted, and all 50° C. samples were amber unless noted.

The invention claimed is:

1. A synergistic microbicidal composition comprising: (a) a nonionic surfactant with structure:

$$R^1O(CH_2CH(CH_3)O)_5(CH_2CH_2O)_9H$$

where $R^1$ is a 2 ethylhexyl group; and (b) a sorbate salt; wherein a weight ratio of said nonionic surfactant to the sorbate salt is from 1:0.1 to 1:0.9143.

* * * * *